United States Patent [19]
Barry

[11] Patent Number: 4,568,191
[45] Date of Patent: Feb. 4, 1986

[54] DISTANCE-INDEPENDENT OPTICAL REFLECTANCE INSTRUMENT

[75] Inventor: Jürgen Barry, Munich, Fed. Rep. of Germany

[73] Assignee: Compur-Electronic GmbH, Munich, Fed. Rep. of Germany

[21] Appl. No.: 510,454

[22] Filed: Jul. 1, 1983

[30] Foreign Application Priority Data

Jul. 14, 1982 [DE] Fed. Rep. of Germany ....... 3226372

[51] Int. Cl.⁴ .......................................... G01N 21/47
[52] U.S. Cl. .................................................. 356/446
[58] Field of Search ............................... 356/445, 446

[56] References Cited

U.S. PATENT DOCUMENTS

| | | | |
|---|---|---|---|
| 3,396,280 | 8/1968 | Knudsen | 356/445 X |
| 3,473,878 | 10/1969 | Schweitzer | 356/446 |
| 3,718,399 | 2/1973 | Kalman | 356/448 |
| 3,806,256 | 4/1974 | Ishak | 356/227 X |
| 3,877,818 | 4/1975 | Button et al. | 356/445 X |
| 4,029,420 | 6/1977 | Simms | 356/446 |
| 4,464,054 | 8/1984 | Karras et al. | 250/227 X |

Primary Examiner—Vincent P. McGraw
Attorney, Agent, or Firm—Townsend and Townsend

[57] ABSTRACT

In known apparatus for taking reflectance readings the accuracy is very highly dependent on the distance between the transmitter and/or receiver area, on the one hand, from the surface whose reflectance is to be measured on the other. In the invention, in the field of measurement, the beam from a transmitter has superimposed on it the beam of at least one further transmitter so that within a wide range of operation readings are made independent of the distance between the said field on the one hand and the transmitter and/or receiver plane on the other and for this reason there is a deep range of measurement, that is to say compensation of depth. Preferably the transmitters are placed axially symmetrically with respect to the axis of the received beam (beam coming from the sample) or planarly symmetrical with respect to a plane containing the axis of the said beam.

14 Claims, 12 Drawing Figures

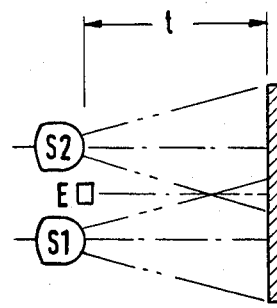
FIG. 1
FIG. 2
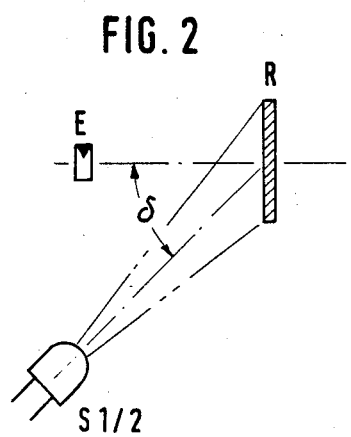
FIG. 3
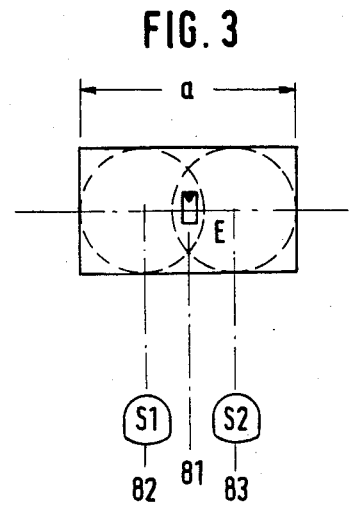
FIG. 5
FIG. 7
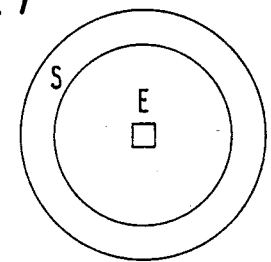
FIG. 6
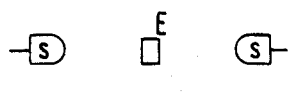
FIG. 8
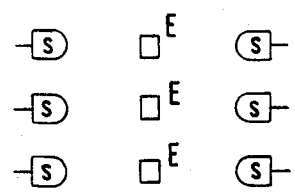

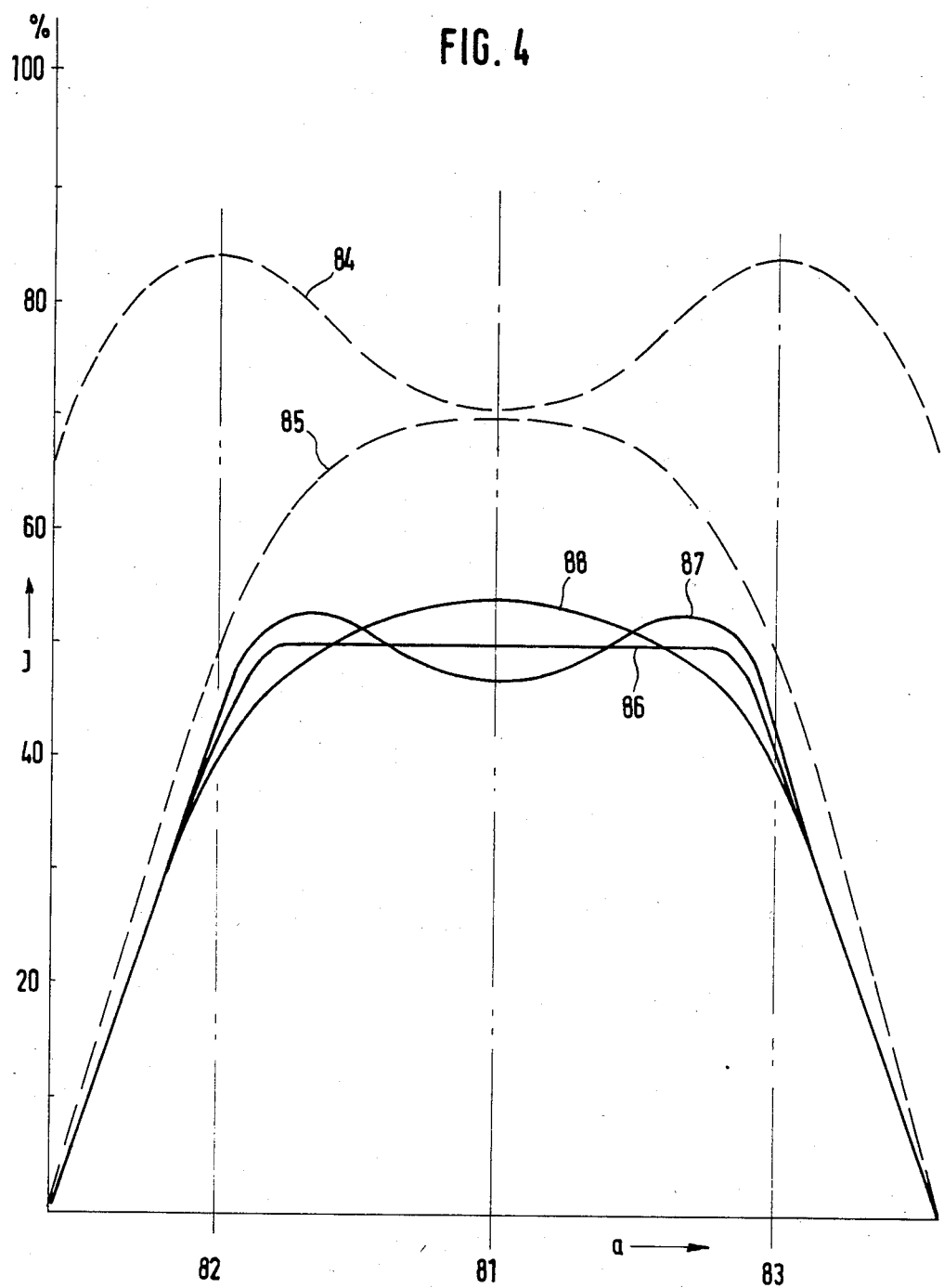

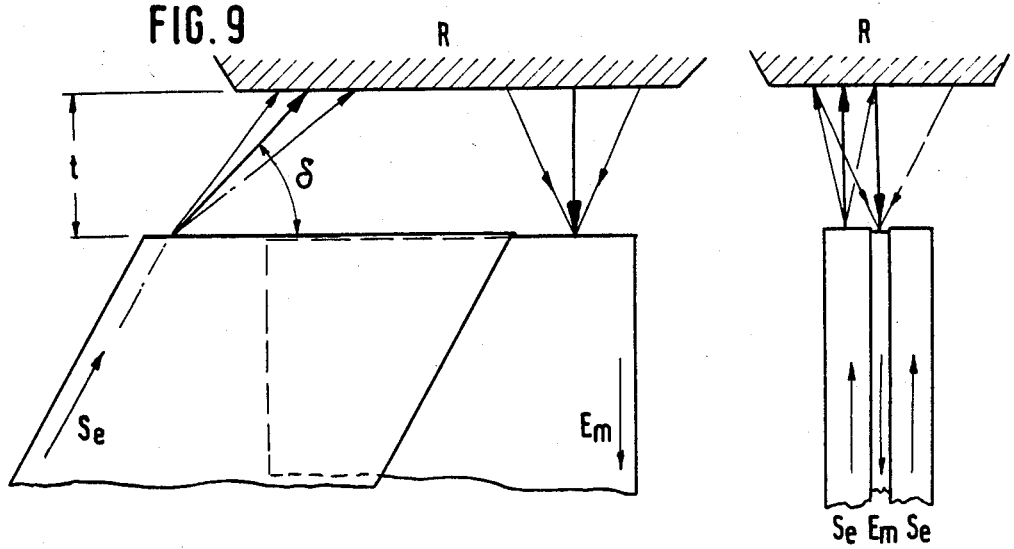
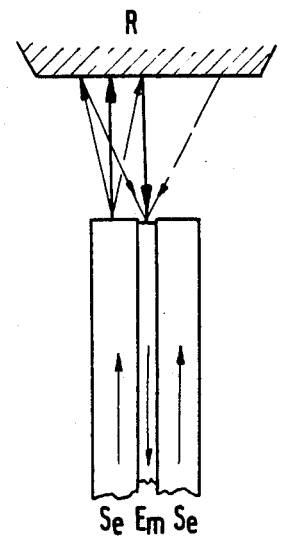
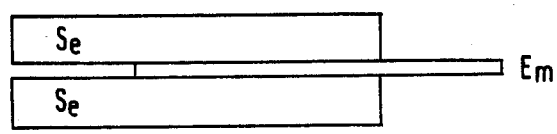
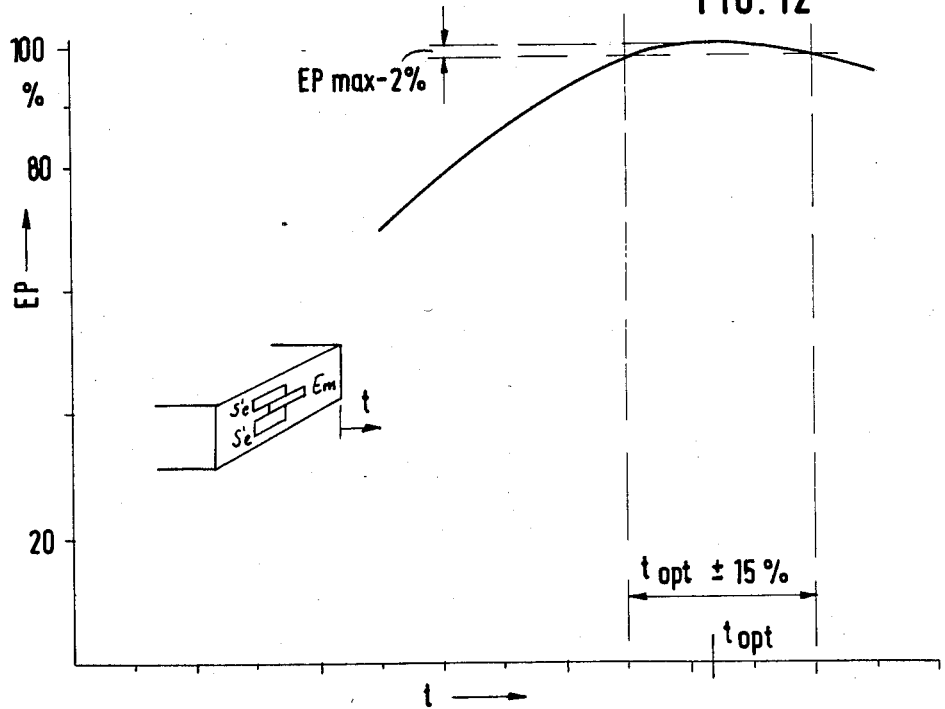

DISTANCE-INDEPENDENT OPTICAL REFLECTANCE INSTRUMENT

BACKGROUND OF THE INVENTION

The present invention is with respect to a way of measuring reflectance of radiation at a reflecting surface in a field of measurement, using a transmitter producing a beam of radiation and a receiver for the beam after undergoing reflectance. Furthermore the invention has to do with forms of apparatus for measuring reflectance at a reflecting surface using a transmitter and a receiver.

Reflectance measurements are undertaken for the purpose of measuring reflectance of light reflecting surfaces so that readings may be taken for such reflectance or changes therein and a quantitative record may be produced. Measurements of this sort, to be exact, have so far been very greatly dependent on the distance the reflectance surface to be tested, that is to say from the distance the field of measurement is from the transmitter and/or the receiving surface. Because the reading produced for the intensity of the reflected beam and for this reason the outcome of measurement is very highly dependent on the distance between the reflectance surface or the field of measurement and the transmitter and/or the receiving surface, in the case of normal or prior art processes and apparatus for reflectance measurement a question of key importance is having the surface to be tested or measured (that is to say the field of measurement) at a highly reproducible distance from the receiver and/or the transmitter. In the case of a known reflectance photometer (see German Offenlegungsschrift specification No. 3,011,223) very complex means had to be used for keeping to the desired distance between the field of measurement and the receiver or transmitter and for making certain that exact adjustment to this distance was possible on setting up the apparatus. The use of such a known apparatus is very complex and only well trained persons come into question for the operation thereof, and even so there is still the danger of false readings being taken.

SHORT OUTLINE OF THE INVENTION

It is for this reason that one purpose or object of the present invention is designing a process and forms of apparatus for the measurement of reflectance with which true reflectance readings may be taken simply and without a complex apparatus having to be used.

A still further purpose of the invention is to make this possible without having to keep to narrow tolerances in the distance between the transmitter and/or the receiver on the one hand and the field of measurement on the other.

For effecting these and further purposes that will become clear on reading further parts of the present account, a way of measuring in keeping with the present invention is characterized in that in the field of measurement the beam of a first transmitter has at least partly superimposed thereon a beam of at least one further transmitter.

For an account of the scientific idea on which the present invention is based use is now to be made of FIGS. 1, 2 and 3 herein.

These figures are three views of an apparatus made up of a receiver and two transmitters S1 and S2, the transmitters S1 and S2 being placed symmetrically in relation to the receiver and at an equal distance therefrom. In FIG. 4 the geometrical placing of the receiver and the transmitters of FIG. 3 is marked again along the horizontal axis, number 81 being used for the axis of the receiving beam and numbers 82 and 83 for the transmitting beam axes of the two transmitters S1 and S2. The receiving or illumination levels are marked along the upright axis. The curve 84 is the function of the illumination or level distribution, that is formed by the superimposition or addition of the illumination functions of the two transmitters S1 and S2. The receiving function or receiving level distribution of the receiver E is marked 85.

The functions or curves 84 and 85 are the illumination function in the one case and the receiving function in the other at a distance t of the reflectance surface R, as will be seen from FIG. 1. By the putting together of these two functions 84 and 85 an overall or total function 86 is produced, in which the values of the illumination and receiving functions 84 and 85 are multiplied at every point on the horizontal axis. The functions 84, 85 and 86 are produced for an optimum distance $t_{opt}$ of the surface R whose reflectance is to be measured from the transmitters S1 and S2 and/or from the receiver E.

If the surface R whose reflectance is to be measured or the field of measurement is at a distance t from the transmitting and/or receiving plane that is not the optimum distance $t_{opt}$ the overall functions will be changed in form as well.

If the distance t of the field of measurement R from the transmitting and/or receiving plane is smaller than the optimum distance $t_{opt}$ there is in this case a more marked dent in the middle of the illumination function 84 because of the smaller distance. Furthermore when $t < t_{opt}$, there is a lower overall intensity of illumination because of this change in form of the illumination function 84.

When things are the other way round and $t > t_{opt}$, the illumination function 84 has a smaller dent. Furthermore when t is greater than $t_{opt}$ there is a greater overall intensity of illumination because of this change in form of the illumination function 84.

An intensity measured by the receiver when the distance t is smaller than the optimum distance $t_{opt}$ of the field R of measurement from the transmitter and/or receiver plane is greater and the other way round. That is to say, with respect to the overall intensity of illumination, the intensity measured by the receiver undergoes a change opposite to any change made in the distance of the field R of measurement from the transmitter and/or receiver plane.

Taking an overall view, it may be said that when t is less than $t_{opt}$ there is an overall function 87 with a dent in the middle whereas when t is greater than $t_{opt}$ there is an overall function 88 with an upward bulge.

However on making a comparison of the surface integrals of the overall functions 86, 87 and 88 for the said cases, it will be seen that the integrals are generally equal whereas the distances of the field of measurement from the transmitter and/or receiver plane are different. That is to say, for the different values of the distance of the field of measurement from the transmitter and/or receiver plane generally the same intensity is measured by the receiver, or in other words, any difference in the distance between the field R of measurement and the transmitter and/or receiver plane has no or hardly any effect on the reading, at least in a certain range of operation and the reading may be said to be in substance independent of the distance of the field of measurement from the transmitter and/or receiver plane.

As will now be clear, this depth compensation is made possible by the use in the invention of two transmitters in connection with one receiver.

The system with the two transmitters in connection with the receiver does not have to be symmetrical in all cases. Given an asymmetrical placing of the transmitters and the receiver, one will then have asymmetrical illumination and receiving functions or characteristics and for this reason asymmetrical overall functions as well.

In keeping with a preferred development of the present invention the transmitters S1 and S2 are each placed symmetrically, that is to say at the same distance from the receiver, the symmetrical form of the function curves then being produced as in FIG. 4.

Taking as a starting point a known apparatus for measuring reflectance at a reflecting surface, and using a transmitter and a receiver, the purpose of the invention may furthermore be effected by having at least one further transmitter that is placed generally axially symmetrically with respect to the received beam axis.

In keeping with a preferred form of the invention the transmitted beam axes are at an angle $\alpha$ to the received beam axis, the angle $\alpha$ being greater than 0° but less than or equal to (or not greater than) 90°. More specially the angles $\alpha$ are of equal size so that there is angular symmetry. It is however furthermore possible for the transmitted beam axes to be at different angles.

As part of a further preferred working form of the apparatus of the present invention the transmitters are placed in a ring about the axis of the received beam. In this respect there is a free selection of the number of transmitters, the spacing of same from each other preferably being equal. The greater the number of transmitters placed in a ring about the axis of the received beam, the less the effect of surface grain or structure of the sample (as for example in the case of textile materials) on the readings. In this respect one form of the invention that is more specially useful is one in which in place of having separate transmitters a single one in the form of a ring is used, that is placed generally axially symmetrically with respect to the axis of the received beam.

A further useful effect is to be had if in place of an axially symmetrical system of the transmitters, they are placed generally symmetrically with respect to a plane in which the received beam axis is placed.

In keeping with a still further preferred form of the invention the transmitted beam axes are at a generally equal angle $\alpha$ to the axis of the received beam, $\alpha$ being greater than 0° and less than or equal to 90°.

As a more specially useful form of the invention the transmitted beam axes are generally parallel to each other and are at an angle $\alpha$ to the received beam axis, the angle $\alpha$ being greater than 0° and less than or equal to 90°.

If the sample to be tested is long and narrow in form, it is furthermore possible as part of the invention to have at least two receivers each with two transmitters placed symmetrically in relation thereto, the receivers being placed in a single plane. Dependent on the conditions and needs of a given case, it is only the radiation of those transmitters placed for use with a given receiver that will be received by such a receiver, or radiation of transmitters may be received, that are placed for use with receivers next to said given receiver.

The purpose of the invention may furthermore be effected with forms of apparatus in the case of which the transmitters and the receivers are changed over in position in relation to each other. In the case of the apparatus as noted hereinbefore having two transmitters placed symmetrically in relation to a receiver, the outcome of such a change-over would be that two receivers are in each case placed symmetrically in relation to one transmitter. The general conditions and teachings of the invention would be still be kept to in this case as well.

The process and the forms of the apparatus in keeping with the present invention may be used for making acoustic measurements and furthermore for measuring using electromagnetic radiation such as light.

A detailed account will now be given of some forms of the invention by way of example using the figures in connection with the measurement of reflectance using light.

LIST OF DIFFERENT VIEWS OF THE FIGURES

FIG. 1 is a diagrammatic view of a system with one receiver and two transmitters as seen from above.

FIGS. 2 and 3 are side views of the system to be seen in FIG. 1.

FIG. 4 is a graph with functions to make clear the workings of the present invention.

FIG. 5 is a view looking down on a system with two transmitters placed axially symmetrically about one receiver.

FIG. 6 is a view looking down onto a system in which four transmitters are placed axially symmetrical about one receiver.

FIG. 7 is a diagrammatic view of a system, in which a ring-like transmitter is placed round one receiver.

FIG. 8 is a diagrammatic view of an apparatus made up of a number of systems as seen in FIG. 1 placed in rows for measuring reflectance from long narrow fields of mesurement or samples.

FIGS. 9 to 11 are views of a form of the invention on the same lines as that of FIGS. 1 to 3 with light fiber guides in a number of different views.

FIG. 12 is a a received signal level curve as a function of the distance of the field of measurement from the transmitting and receiving plane for the working example of the invention to be seen in FIGS. 9 to 11.

DETAILED ACCOUNT OF WORKING EXAMPLES OF THE INVENTION

As noted at an earlier stage in the present specification, the form of the invention of FIGS. 1 to 3 has only one receiver and two transmitters, that are placed symmetrically with respect to a plane containing the axis of the received beam. A side view of the system of FIG. 1 will be seen in FIG. 3, this making clear the overlap of the transmitting levels on the reflectance surface. t is the distance between the surface R whose reflectance is to be measured from the transmitter and receiver plane. In this connection it is to be noted that the receiver plane is not necessarily the same or lined up with the transmitter plane. Forms of the invention would in fact be possible in which the receiver plane would be at a distance from the reflectance sample surface R such that it would be nearer thereto or further therefrom than the transmitter plane.

FIG. 4 is presented to make clear the general theory of the workings of the present invention and an account has been given earlier herein.

FIG. 5 is a view of a simple form of the invention with two transmitters and one receiver, about which the two transmitters are placed so as to be generally axially symmetrical thereto.

In FIG. 6 the reader will see a receiver E, that has four transmitters placed about it in a generally axially symmetrical system. It would naturally be possible as well for there to be more than four transmitters placed axially symmetrically about the receiver.

A specially useful working example of the invention is to be seen in FIG. 7, in the case of which there is a ring-like transmitter placed axially symmetrically round one receiver, a ring-like transmitter offering the useful effect that no lining up of separate transmitters in relation to each other is necessary so that one then has a highly simple and nevertheless efficient measuring apparatus or system, in which surface grain or structure, as for example in the case of textiles, does not have any effect on the readings.

It is more specially in the case of measurement of the reflectance of long narrow samples, as for example test strips for medical purposes, that the system to be seen in FIG. 8 has turned out to give good effects. In this system a number of receivers are placed in one plane, each receiver having two transmitters for use therewith. The separate transmitters may furthermore be place in the form of a transmitter tube each on the two sides of the receivers so that the number of single transmitters is cut down and there is then a simpler and lower-price measuring apparatus. For certain uses the receivers placed in a line may designed as a single receiving tube.

In FIGS. 9 to 11 the reader will see a working example of the invention based on the diagrammatically presented system of FIGS. 1 to 3 using light fiber guides. This working example of the invention is specially designed for measuring reflectance in cases in which the transmitted light beam comes to the surface whose reflectance is to be measured at an angle of $\delta$ equal to 45° and the reflected light beam from the reflectance surface comes to the received light guide Em normally (this being the so-called 45°-0° measuring system). The transmitted and received light guides Se and Em are in a sort of sandwich structure so that the system takes up very little space.

FIG. 12 is a graph to make clear the changes in the received light level EP as a function of the distance t of the field of measurement from the transmitting and receiving planes. The distance of the field of measurement from the transmitter or receiver plane, at which the reading for the received signal $EP_{max}$ is greatest, is marked along the horizontal axis as $t_{opt}$. On changing the position of the field of measurement so as to be different to the optimum distance $t_{opt}$ by up to 15% either way, the change in the received level is only 2% of the greatest received level $EP_{max}$. This will at once make it clear that the value of the measurement or reading only undergoes quite small changes over a relatively wide working range. In other words, the measuring apparatus in keeping with the present invention makes possible depth compensation, and over a wide working range the reflectance reading will not be dependent on the exact distance of the field of measurement from the receiving and transmitting plane. This being the case, it is furthermore not necessary to keep to exact settings for the distance between the receiver and transmitter plane on the one hand and the surface in the field of measurement on the other, that is to say, it is not necessary for such distance settings to be very exactly reproduced. The sample furthermore does not have to be of the same thickness and may be bent or twisted without this producing any undesired effect on the readings. This property makes the new system more specially of value when taking reflectance readings on medical test strips, inasfar as one and the same measuring apparatus may be used on test strips of different thickness without having any effect on the readings.

Furthermore the reflectance measuring apparatus of the present invention is more specially of value for measuring the reflectance of band or tape material that is kept on the move and running past the reflectance measuring head even while readings are being taken, as for example in the paper making and textile industries, inasfar as no special attention has to be given to keeping to an unchanging distance between the instrument head and the material that is to be tested.

Although the account hereinbefore of the invention has been limited to a small number of special working forms thereof, it will be clear to those in the art that a great number of different developments and outgrowths of the teaching of the process and apparatus of the invention will be possible and that different uses thereof are possible with giving up the key teachings and ideas of the invention.

I claim:

1. A process for measuring reflectance at the surface of a plurality of samples using a transmitted beam from a transmitter and using a receiver receiving a reflected beam from said sample comprising:
   transmitting beams from at least two transmitters to one of said samples;
   arranging said transmitters so that said beams are at least partially superimposed on a surface of said sample where said beams impinge;
   receiving a reflected beam from said sample with said receiver; and
   positioning said samples so that the distance from each said sample to said receiver varies substantially from sample to sample.

2. The process of measurement as claimed in claim 1 wherein the beams that are superimposed on each other are in substance symmetrical in relation to an axis of the received beam.

3. The process of claim 1 wherein said distance from said sample to said receiver varies from an optimum distance at which the intensity of said reflected beam at said receiver is a maximum by a maximum of 15% of said optimum distance.

4. An apparatus for the measurement of reflectance at the surface of a sample, comprising:
   a transmitter for directing a transmitted beam towards said sample;
   a receiver for receiving radiation coming from said sample after undergoing reflectance on a surface thereof;
   a further transmitter placed generally axially symmetrically with respect to an axis of said received beam such that beams from said transmitters are superimposed on a portion of said surface of said sample; and
   means for passing a plurality of said samples past said transmitters such that a distance from said receiver to said surface of said sample varies substantially from sample to sample.

5. The apparatus as claimed in claim 4 wherein the axes of said transmitted beams are at an angle $\alpha$ to the axis of said received beam, said angle α being greater than 0° and not greater than 90°.

6. The apparatus as claimed in claim 4 wherein said transmitters are placed on a ring running round said axis of said received beam.

7. The apparatus as claimed in claim 4 comprising a ring-like transmitter placed round said axis of said received beam.

8. The apparatus as claimed in claim 4 wherein the transmitters are changed over in position to be in the position of the receiver and the receiver and changed over so as to be in the positions of the transmitters.

9. An apparatus for measuring reflectance at the surface of a sample comprising:
   a transmitter for directing radiation onto said sample;
   a receiver for receiving a beam of such radiation after reflectance at said sample;
   at least one further transmitter placed generally symmetrically in a plane containing an axis of said received beam, said further transmitter being placed such that beams from said transmitters are superimposed on a portion of a surface of said sample; and
   means for passing a plurality of said samples past said transmitters such that a distance from said receiver to said surface of a sample passing said transmitters varies substantially from sample to sample.

10. The apparatus as claimed in claim 9 wherein axes of said transmitted beams are each at an angle α to the axis of the received beam, said angle α being greater than 0° and not greater than 90°.

11. The apparatus as claimed in claim 9 wherein the axes of the transmitted beams are generally parallel to each other and are at an angle α to the axis of the received beam, the angle α being greater than 0° and not greater than 90°.

12. The apparatus as claimed in claim 9 comprising at least two such receivers placed in a row.

13. The apparatus of claim 9 wherein said distance from said sample to said receiver varies from an optimum distance at which the intensity of said beam at said receiver is a maximum by a maximum of 15% of said optimum distance.

14. A process for measuring reflectance at the surface of a plurality of samples using a transmitted light beam from a plurality of transmitters and using a receiver receiving a reflected beam from a surface of each said sample such that said measured reflectance is substantially insensitive to variations in a distance between said receiver and said sample surface, comprising:
   transmitting light beams from at least two transmitters to one of said samples;
   arranging said transmitters so that said beams are superimposed over at least a portion of said surface of said sample;
   receiving a reflected beam from said sample with said receiver;
   moving said samples past said transmitters and receivers such that said surface of said samples is near an optimum distance from said receiver where said reflected beam has a maximum intensity; and
   permitting the distance from said receiver to said surface of said samples to vary relative to said optimum distance over a range of up to 15% of said optimum distance.

* * * * *